United States Patent
Kojima

(10) Patent No.: US 11,540,713 B2
(45) Date of Patent: Jan. 3, 2023

(54) KERATOCONUS DETERMINATION APPARATUS AND STORAGE MEDIUM

(71) Applicant: CHUKYO MEDICAL CO., INC., Nagoya (JP)

(72) Inventor: Takashi Kojima, Nagoya (JP)

(73) Assignee: CHUKYO MEDICAL CO., INC., Nagoya (JP)

( * ) Notice: Subject to any disclaimer, the term of this patent is extended or adjusted under 35 U.S.C. 154(b) by 285 days.

(21) Appl. No.: 16/805,563

(22) Filed: Feb. 28, 2020

(65) Prior Publication Data

US 2020/0288964 A1 Sep. 17, 2020

(30) Foreign Application Priority Data

Mar. 13, 2019 (JP) .............................. JP2019-045345

(51) Int. Cl.
*A61B 3/10* (2006.01)
*A61B 3/107* (2006.01)
(Continued)

(52) U.S. Cl.
CPC ............ *A61B 3/107* (2013.01); *A61B 3/0025* (2013.01); *A61B 3/103* (2013.01); *A61B 3/1035* (2013.01)

(58) Field of Classification Search
CPC ..... A61B 3/0025; A61B 3/103; A61B 3/1035; A61B 3/107
(Continued)

(56) References Cited

U.S. PATENT DOCUMENTS

2003/0236470 A1* 12/2003 Falck, Jr. ................. A61B 3/16
600/558
2005/0225724 A1 10/2005 Klyce et al.
(Continued)

FOREIGN PATENT DOCUMENTS

EP 3056906 A1 8/2016
JP 61-146227 A 7/1986
(Continued)

OTHER PUBLICATIONS

Office Action for Japanese Application 2019-045345, dated Feb. 5, 2020 with English Machine Translation.
(Continued)

*Primary Examiner* — Mahidere S Sahle
(74) *Attorney, Agent, or Firm* — Kenichiro Yoshida

(57) ABSTRACT

Provided are an apparatus and a computer-readable storage medium having stored therein a program that can determine keratoconus with a simple configuration so as to allow the apparatus and the program to be distributed widely and contribute to early diagnosis of keratoconus. In a keratometer as a keratoconus determination apparatus, a prediction model for keratoconus is stored in a memory. The prediction model is a logistic regression model in which three parameters that are a steep meridian refractive power, a flat meridian refractive power, and a value indicating whether or not a subject eye has a with-the-rule astigmatism, are independent variables, and a probability of keratoconus is a dependent variable. A control unit substitutes the three parameter values into the prediction model, to obtain a probability of keratoconus. When the probability is greater than a cutoff value, the subject eye is determined to be suspected of having keratoconus.

5 Claims, 2 Drawing Sheets

(51) Int. Cl.
*A61B 3/00* (2006.01)
*A61B 3/103* (2006.01)

(58) Field of Classification Search
USPC ........................................ 351/205, 206, 212
See application file for complete search history.

(56) References Cited

U.S. PATENT DOCUMENTS

| | | | |
|---|---|---|---|
| 2013/0188140 A1 | 7/2013 | Bagherinia et al. | |
| 2014/0043588 A1* | 2/2014 | Grant .................... | G02C 7/049 351/247 |
| 2017/0181620 A1* | 6/2017 | Andrews ............... | A61B 3/1035 |
| 2020/0100673 A1* | 4/2020 | Shimizu ................. | A61B 3/14 |

FOREIGN PATENT DOCUMENTS

| | | |
|---|---|---|
| JP | 2005-288176 A | 10/2005 |
| JP | 2007-7215956 A | 8/2007 |
| JP | 2011-167359 A | 9/2011 |

OTHER PUBLICATIONS

"Indoor Visit Detection Technics With Sensors of Smartphones and Machine Learning" by Hiromi Minakaimi et al., as appears in "Muti-media, Decentralized, Cooperative and Mobile (DICOMO 2017) Symposium" Proceedings IPSJ Symposium Series of Jun. 2017, No. 1, pp. 991-994, with English Machine Translation.

European Search Report dated Jul. 30, 2020 for the corresponding EP patent application, 20161967.3-1122.

EP Communication dated Oct. 20, 3033 for corresponding EP patent application No. 20 161 967.3.

Sideroudi Haris et al: "Fourier analysis of videokeratography data: Clinical usefulness in grade I and subclinical keratoconus," Journal Cataract and Refractive Surgery, Surgery, Fairfax, VA, US, vol. 42, No. 5, May 30, 2016 (May 30, 2016), pp. 731-737, XP029561525, ISSN:0886-3350, DOI: 10.1016/J.JCRS.2016.01.049.

Martinez-Abad Antonio et al: "Evaluation of the diagnostic ability of vector parameters characterizing the corneal astigmatism and regularity in clinical and subclinical keratoconus," Contact Lens and Anterior Eye, Stockton Press, Basingstoke, GB, vol. 40, No. 2, Dec. 5, 2016 (Dec. 5, 2016), pp. 88-96, XP029953139, ISSN: 1367-0484, DOI: 10.1016/J.CLAE.2016.11.008.

Kenichiro Bessho et al: "Automated Keratoconus Detection Using Height Data of Anterior and Postenor Corneal Surfaces," Japanese Journal of Ophthalmology; the Official English-Language Journal ot The Japanese Ophthalmological Society, Springer-Verlag, TO, vol. 50, No. 5, Sep. 1, 2006 (Sep. 1, 2006), pp. 409-416, XP019432535, ISSN: 1613-2246, DOI: 10.1007/S10384-006-0349-6.

* cited by examiner

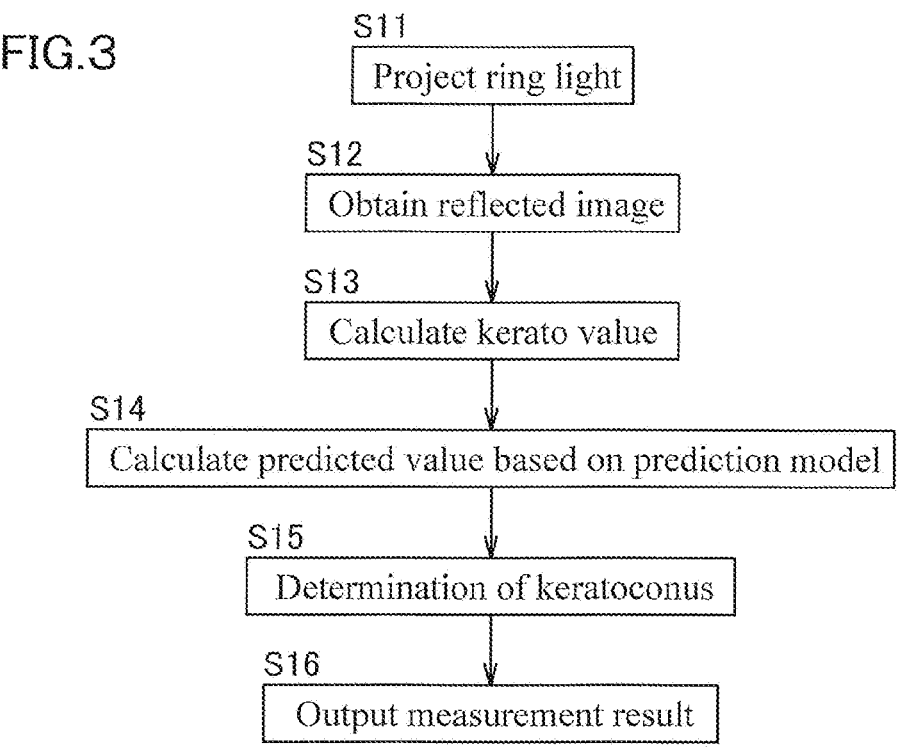
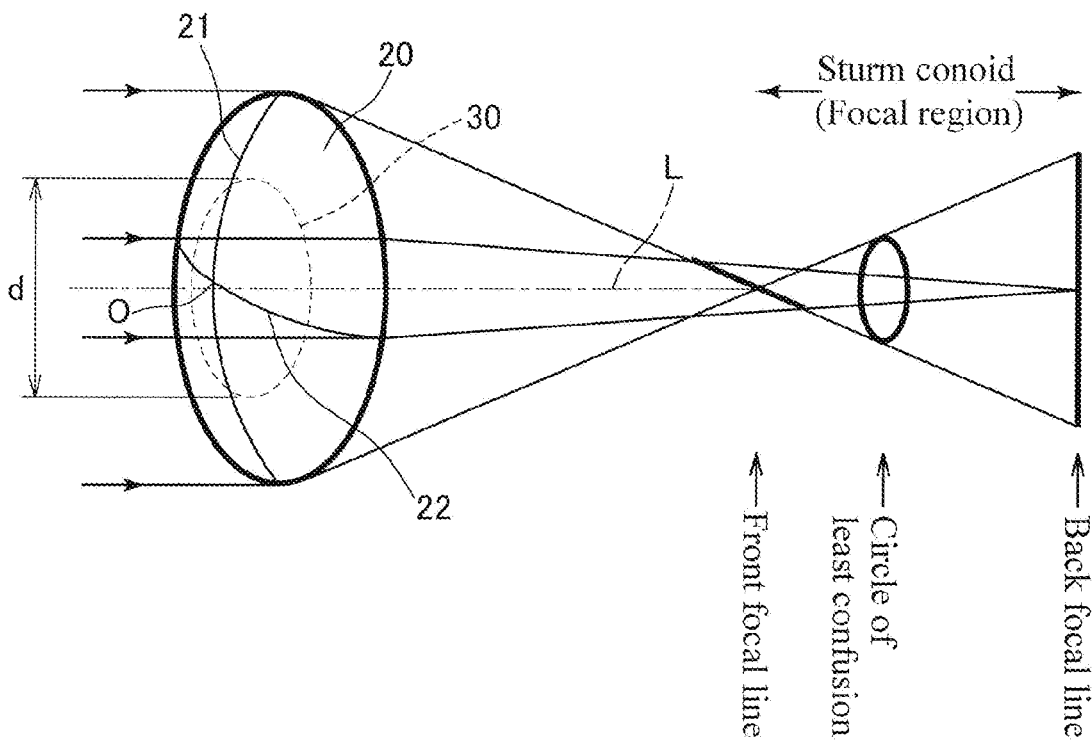

KERATOCONUS DETERMINATION APPARATUS AND STORAGE MEDIUM

RELATED APPLICATIONS

This application claims the priority of Japanese Patent Application No. 2019-045345 filed on Mar. 13, 2019, which is incorporated herein by reference.

BACKGROUND OF THE INVENTION

Field of the Invention

This disclosure relates to a keratoconus determination apparatus for determining keratoconus which is one kind of eye disease.

Description of Related Art

Keratoconus is one kind of eye disease. Keratoconus is a disease in which the center portion of a cornea becomes thin, and the cornea projects forward so as to have a conical shape. The patients develop keratoconus in their teens and twenties in many cases, and keratoconus is a progressive disease. Unless appropriately treated, the cornea is greatly distorted, and cannot be corrected with eyeglasses, thus requiring corneal transplant in some cases. Therefore, early diagnosis and early treatment are important. Recently, corneal crosslinking procedure as a progress preventing therapy at the early stage is becoming the standard of the therapy.

Early diagnosis of keratoconus has been performed by corneal shape analysis (corneal topography), and it is known that the diagnostic rate is high. In the corneal shape analysis, for example, based on positional information of a ring image (Placido ring image) obtained by projecting multiple ring light beams concentrically on the cornea, a curvature of the cornea is obtained at a portion on which the ring light is projected, to obtain the surface shape of the cornea (for example, see Japanese Laid-Open Patent Publication No. 2011-167359). In the corneal shape analysis, for example, curvatures are measured at a plurality (for example, 256) of portions in the circumferential direction for each of a plurality of radial positions which are distant from the center of the cornea over different radial distances, thereby obtaining a three-dimensional shape of the surface (anterior surface) and the posterior surface of the cornea. It is also known that, as one kind of the corneal shape analysis, analysis of shapes of the anterior surface and the posterior surface of the cornea with the use of anterior segment OCT (optical coherence tomography) is performed.

Meanwhile, other than the above-described corneal shape analyzer, an auto keratometer is known as a device for measuring a parameter related to a corneal shape. The auto keratometer is, for example, a test device that projects, on a corneal surface, ring light or a plurality of dot-like light beams which are arranged into a ring-like shape, and that measures, based on the reflected image, a curvature radius of each of the steep meridian and the flat meridian, a refractive power, and the direction (angle) of each meridian at a position at a predetermined radius (for example, about 3 mm radius) on the corneal surface (for example, see Japanese Laid-Open Patent Publication No. S61-146227, Japanese Laid-Open Patent Publication No. 2007-215956).

SUMMARY OF THE INVENTION

Keratoconus is definitively diagnosed by corneal shape analysis (corneal topography). However, the corneal shape analyzers are installed merely in some special hospitals for corneas and large hospitals, and have not been distributed widely for general medical practitioners. Therefore, when keratoconus is diagnosed by the corneal shape analysis, the keratoconus may have already progressed to an initial (early) or later stage.

This disclosure has been made in view of the aforementioned circumstances, and an object of this disclosure is to provide an apparatus that can determine keratoconus with a simple configuration, and a computer-readable storage medium having stored therein a program that can determine keratoconus so as to allow the apparatus and the program to be distributed widely and contribute to early diagnosis of keratoconus.

This discloser aims at development of keratoconus risk diagnosis software to be installed in an auto keratometer with placing focus on an auto keratometer installed at any ophthalmologist's office. This discloser has generated a regression equation in which parameters which can be measured by an auto keratometer in multiple logistic regression analysis, specifically, a refractive power at a steep meridian of a cornea, a refractive power at a flat meridian of the cornea, and a direction (angle) of the steep meridian are set as independent variables, and a value indicating likelihood of keratoconus is set as a dependent variable, and has found that presence or absence of keratoconus can be determined with high accuracy by the regression equation, and has completed this disclosure.

Specifically, a keratoconus determination apparatus according to one aspect of this disclosure includes:

an obtaining portion configured to obtain at least two values among a refractive power or a curvature radius at a steep meridian of a cornea of an eye to be tested, a refractive power or a curvature radius at a flat meridian of the cornea, and an angle of the steep meridian or the flat meridian; and a determination portion configured to determine whether or not the eye to be tested has keratoconus, based on the values obtained by the obtaining portion.

Thus, keratoconus can be determined by at least two parameters obtained by the obtaining portion, and the entire shape of the cornea need not be measured, so that keratoconus can be determined with a simple configuration. When "the refractive power or the curvature radius at the steep meridian" is a first parameter A, "the refractive power or the curvature radius at the flat meridian" is a second parameter B, and "the angle of the steep meridian or the flat meridian" is a third parameter C, combinations corresponding to "at least two of A, B, and C" are (A, B), (A, C), (B, C), and (A, B, C). The first parameter A is one of the refractive power or the curvature radius at the steep meridian. Two cases, that is, a case where the refractive power at the steep meridian is the first parameter A and a case where the curvature radius of the steep meridian is the first parameter A can be considered. The second parameter B is one of the refractive power or the curvature radius at the flat meridian. Two cases, that is, a case where the refractive power at the flat meridian is the second parameter B and a case where the curvature radius of the flat meridian is the second parameter B can be considered. The third parameter C is one of an angle of the steep meridian or an angle of the flat meridian. Two cases, that is, a case where the angle of the steep meridian is the third parameter C and a case where the angle of the flat meridian is the third parameter C can be considered. Therefore, the number of the parameter combinations corresponding to (A, B) is 2×2=4. The number of the parameter combinations corresponding to (A, C) is 2×2=4. The number of the parameter combinations corresponding to (B, C) is 2×2=4. The number of the parameter combinations corresponding to (A, B, C) is 2×2×2=8. Consequently, the number of the parameter combinations corresponding to at least two of the first parameter A (the refractive power or the curvature radius at the steep meridian), the second parameter B (the refractive power or the curvature radius at the flat meridian), and the third parameter C (the angle of the steep meridian or the flat meridian) is 4+4+4+8=20. When the parameters obtained by the obtaining portion include at least two of the three parameters A, B, and C, the parameters may include a parameter other than the parameters A, B, and C.

Furthermore, according to one aspect of this disclosure, the obtaining portion may obtain all of the refractive power or the curvature radius at the steep meridian of the cornea of the eye to be tested, the refractive power or the curvature radius at the flat meridian of the cornea, and the angle of the steep meridian or the flat meridian, and the determination portion may determine whether or not the eye to be tested has keratoconus, based on all of the refractive power or the curvature radius at the steep meridian, the refractive power or the curvature radius at the flat meridian, and the angle of the steep meridian or the flat meridian, the all thereof being obtained by the obtaining portion. "The obtaining portion obtains all of the refractive power or the curvature radius at the steep meridian of the cornea of the eye to be tested, the refractive power or the curvature radius at the flat meridian of the cornea, and the angle of the steep meridian or the flat meridian" means obtaining the three parameters that are the first parameter A representing one of the refractive power or the curvature radius at the steep meridian, the second parameter B representing one of the refractive power or the curvature radius at the flat meridian, and the third parameter C representing one of the angle of the steep meridian or the angle of the flat meridian.

Thus, all of the three parameters A, B, and C (the refractive power (or curvature radius) at the steep meridian, the refractive power (or curvature radius) at the flat meridian, and an angle of the steep meridian (or the flat meridian)) are used to determine keratoconus, thereby enhancing determination accuracy. In this case, keratoconus may be determined based on only the three parameters A, B, and C. Thus, keratoconus can be simply determined while high determination accuracy is maintained. In addition to the three parameters A, B, and C, another parameter may be used to determine keratoconus. Thus, keratoconus can be determined with enhanced accuracy.

Furthermore, according to one aspect of this disclosure, a storage portion configured to store a relational expression in which the values obtained by the obtaining portion are independent variables, and a value indicating likelihood of keratoconus is a dependent variable, may be provided. The determination portion may determine keratoconus based on the relational expression. In this case, the relational expression may be, for example, a logistic regression equation.

In this case, in the logistic regression equation, for example, a refractive power at a steep meridian of a cornea, a refractive power at a flat meridian of the cornea, and a dummy variable indicating whether an angle of the steep meridian is an angle classified as a with-the-rule astigmatism or another angle may be independent variables, a first coefficient that is a regression coefficient of the refractive power at the steep meridian may be a positive value, a second coefficient that is a regression coefficient of the refractive power at the flat meridian may be a negative value, and a third coefficient that is a regression coefficient of the dummy variable may be a negative value. Furthermore, in this case, for example, the first coefficient may be +1.707, the second coefficient may be −0.997, and the third coefficient may be −3.481. Thus, keratoconus can be determined with enhanced accuracy.

Furthermore, the determination portion may determine whether or not an eye has keratoconus, according to comparison between a predetermined cutoff value and an output value obtained by substituting, into the relational expression, the values obtained by the obtaining portion.

A storage medium according to one aspect of this disclosure is directed to a computer-readable storage medium having stored therein a program for causing a computer to perform: obtaining at least two values among a refractive power or a curvature radius at a steep meridian of a cornea of an eye to be tested, a refractive power or a curvature radius at a flat meridian of the cornea, and an angle of the steep meridian or the flat meridian; and determining whether or not the eye to be tested has keratoconus, based on the values obtained in the obtaining.

Thus, keratoconus can be determined by at least two parameters obtained in the obtaining, and the entire shape of the cornea need not be measured, so that keratoconus can be determined with a simple configuration.

BRIEF DESCRIPTION OF THE DRAWINGS

FIG. 3 is a flow chart showing a process performed by a control unit; and

FIG. 4 shows a state of refraction of light incident on the cornea.

DESCRIPTION OF THE PREFERRED EMBODIMENTS

An embodiment of this disclosure will be described below with reference to the drawings. Firstly, the regression analysis, for keratoconus, which was performed by this discloser will be described with reference to FIG. 1.

Keratometer data of early (mild) keratoconus patients and healthy subjects were collected from multiple facilities. Finally, 124 eyes of 124 early keratoconus patients (86 males, 38 females, the average age was 30.85±15.94 (standard deviation)), and 130 eyes of 130 healthy subjects (82 males, 48 females, the average age was 30.34±6.28) were selected as subjects so as to match the ages (step S1 in FIG. 1). Patients, who were diagnosed as stage 1 of the Amsler-Krumeich classification based on corneal shape analysis, were extracted as the early keratoconus patients.

Figure 1:
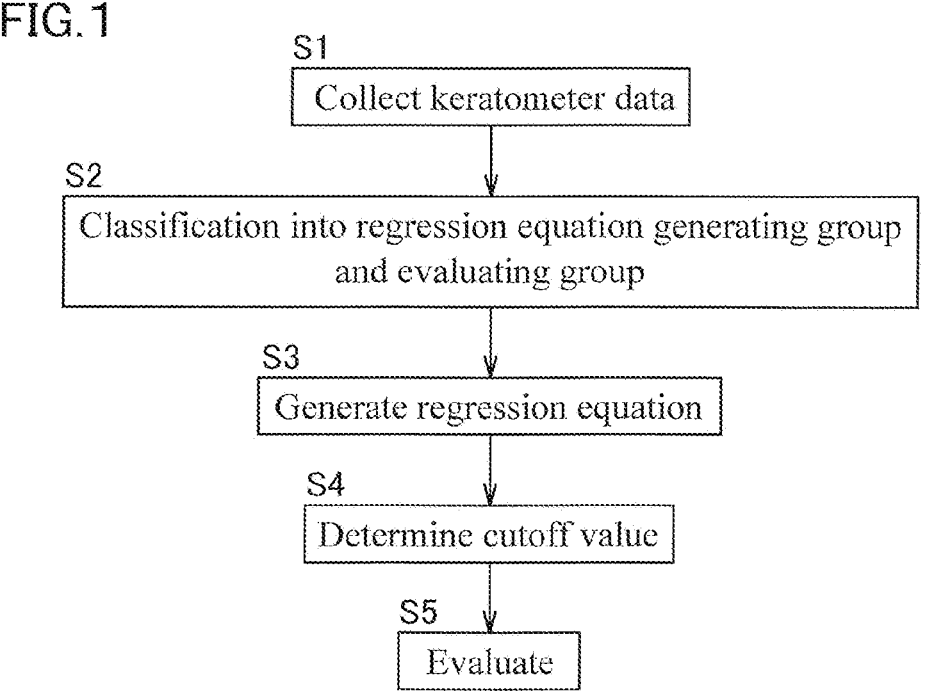
FIG. 1 is a flow chart showing a procedure of generating a prediction model for keratoconus.

Next, the subjects were classified randomly into a regression equation generating group and a regression equation evaluating group such that a ratio in the number of the subjects between the two groups was 2:1 (step S2 in FIG. 1).

Next, multiple logistic regression analysis was performed based on keratometer data of the subjects classified as the regression equation generating group, and data indicating whether or not each subject had keratoconus, to generate a regression equation for predicting whether or not an eye had keratoconus (step S3 in FIG. 1). The regression equation was generated by using statistical analysis software SPSS. Each parameter of the keratometer data, specifically, a steep meridian refractive power, a flat meridian refractive power, an angle of the steep meridian (cornea astigmatic axis direction), a mean refractive power, and a cornea astigmatism power were set as candidate parameters of independent variables (also referred to as explanatory variables) of the regression equation. A value p (0≤p≤1) representing likelihood (probability) of keratoconus was set as a dependent variable (also referred to as response variable) of the regression equation. The probability p of 1 indicated that an eye had keratoconus, and the probability p of 0 indicated a normal case.

In general, the corneal surface is like a toric surface in the case of regular astigmatism. That is, a corneal surface 20 is formed as a curved surface on which a steep meridian 21 that is a meridian having the smallest curvature radius (in other words, the greatest curvature), among meridians that extend along the corneal surface 20 through a corneal center O, is orthogonal, at the center O, to a flat meridian 22 that is a meridian having the greatest curvature radius (in other words, the smallest curvature), as shown in FIG. 4. Light that is incident on the corneal surface 20 and that passes through the steep meridian 21 has a high refractive power. Therefore, the light is greatly refracted, and is collected at a portion in front of the circle of least confusion (at the position of the front focal line in FIG. 4). Meanwhile, the light that passes through the flat meridian 22 has a low refractive power, and the light is not greatly refracted, and is collected at a portion behind the circle of least confusion (the position of the back focal line in FIG. 4).

In the candidate parameters, the steep meridian refractive power is a refractive power (power for refracting light) at the steep meridian 21, at a position 30 at a predetermined diameter d (for example, about 3 mm) with respect to the corneal center O. The flat meridian refractive power is a refractive power at the flat meridian 22 at the position 30. An angle of the steep meridian is an angle of the steep meridian 21 in the case of the horizontal direction (left-right direction of the eye, a direction from one of eyes toward the other of the eyes) being directions of 0 degrees and 180 degrees. An angle of the flat meridian is an angle of the flat meridian 22 in the case of the horizontal direction (left-right direction of the eye) being directions of 0 degrees and 180 degrees, and the angle of the flat meridian is normal to the angle of the steep meridian 21. The mean refractive power represents a mean value of the steep meridian refractive power and the flat meridian refractive power. The cornea astigmatism power represents a difference between the steep meridian refractive power and the flat meridian refractive power.

When the regression equation was generated, the angle of the steep meridian was classified into an against-the-rule astigmatism (greater than or equal to 0 degrees and less than 30 degrees, greater than or equal to 150 degrees and less than 180 degrees), an oblique astigmatism (greater than or equal to 30 degrees and less than 60 degrees, greater than or equal to 120 degrees and less than 150 degrees), and a with-the-rule astigmatism (greater than or equal to 60 degrees and less than 120 degrees) based on the classification of the astigmatism, and a dummy variable (0 or 1) for each astigmatism was assigned. For example, when the angle of the steep meridian was 90 degrees, 0 was assigned to the dummy variable of the against-the-rule astigmatism, 0 was assigned to the dummy variable of the oblique astigmatism, and 1 was assigned to the dummy variable of the with-the-rule astigmatism.

The multiple logistic regression equation is represented by the following equation 1 or equation 2.

$$\text{logit value} = \log(p/(1-p)) = \alpha + \beta_1 x_1 + \beta_2 x_2 + \cdots + \beta_r x_r \quad \text{(Equation 1)}$$

$$p = 1/\{1 + \exp(-(\alpha + \beta_1 x_1 + \beta_2 x_2 + \cdots + \beta_r x_r))\} \quad \text{(Equation 2)}$$

In equation 1 and equation 2, p represents a dependent variable, and represents a probability of occurrence of an event. $x(x_1, x_2, \ldots x_r)$ represents an independent variable. $\alpha$ is a constant. $\beta(\beta_1, \beta_2, \ldots \beta_r)$ represents a regression coefficient.

In the multiple logistic regression analysis, for equation 1 and equation 2, the constant $\alpha$ and the regression coefficients $\beta$ were determined and the independent variables adopted for the regression equation were selected based on the collected actual measurement data. For this case, data indicating whether or not each subject in the regression equation generating group had keratoconus was represented by two values (1 indicated keratoconus, and 0 indicated a normal case), and the constant $\alpha$ and the regression coefficient $\beta$ of each candidate parameter were calculated based on the two-value data and the candidate parameters (the steep meridian refractive power, the flat meridian refractive power, the against-the-rule astigmatism, the oblique astigmatism, the with-the-rule astigmatism, the mean refractive power, and the cornea astigmatism power) for each subject, and the candidate parameters were selected. At this time, the significance level was 5%, and the candidate parameters were selected by using a stepwise method. In the stepwise method, while a fitness of each parameter to the regression model was confirmed, the parameters were sequentially put in or deleted from the regression model one by one. Finally, the parameter was selected such that the p value (significance probability) of the entire regression model was less than the significance level (5%).

As a result of the multiple logistic regression analysis, the parameters selected as the independent variables were the steep meridian refractive power $x_1$, the flat meridian refractive power $x_2$, and a dummy variable $x_3$ indicating whether the angle of the steep meridian was classified as a with-the-rule astigmatism or the other ones. The other parameters, specifically, the mean refractive power, the cornea astigmatism power, the dummy variable indicating whether or not the angle was classified as an against-the-rule astigmatism, and the dummy variable indicating whether or not the angle was classified as an oblique astigmatism were not adopted in the regression model at that time. The regression coefficient $\beta_1$ of the steep meridian refractive power $x_1$ was +1.707, the regression coefficient $\beta_2$ of the flat meridian refractive power $x_2$ was -0.997, the regression coefficient $\beta_3$ of the dummy variable $x_3$ for the with-the-rule astigmatism was -3.481, and the constant $\alpha$ was -30.791. That is, as the regression equation, the following equation 3 was derived. The p value (significance probability) of the entire regression model represented by equation 3 was less than 0.001 (less than 0.1%)

$$\text{logit value} = \log(p/(1-p)) = -30.791 + 1.707 x_1 - 0.997 x_2 - 3.481 x_3 \quad \text{(Equation 3)}$$

An odds ratio of the steep meridian refractive power $x_1$ was 5.510, an odds ratio of the flat meridian refractive power $x_2$ was 0.369, and an odds ratio of the dummy variable $x_3$ for the with-the-rule astigmatism was 0.031.

The logit value can be converted to the probability p of occurrence of keratoconus by using the formula of the inverse conversion of the logistic as indicated in equation 4.

$$p = \exp(\text{logit value})/(1 + \exp(\text{logit value})) \quad \text{(Equation 4)}$$

Returning to FIG. 1, after the regression equation indicated by equation 3 was generated in step S3, a cutoff value (threshold value) for determining whether or not an eye was suspected of having keratoconus was determined (step S4). The cutoff value was obtained as follows. That is, firstly, a ROC curve (receiver operatorating characteristic curve) was drawn. The ROC curve was obtained by plotting points of the positive case rate and the false positive case rate in the case of the cutoff value being changed, when the horizontal axis represented the false positive case rate (1-specificity) and the vertical axis represented the positive case rate (sensitivity). The sensitivity (positive case rate) represented a ratio of the number of persons each determined as having a disease relative to the number of persons who received a test in which a group of patients having a specific disease was tested for presence or absence of the disease (that is, a ratio of the number of persons of the positive case determined correctly as being positive). The specificity represented a ratio of the number of persons each determined not to have a disease relative to the number of healthy subjects who received a test in which a group of healthy subjects who did not have a specific disease was tested for the presence or absence of the disease (that is, the ratio of the number of persons of the negative case determined correctly as being negative). The false positive case rate (1-specificity) represented a ratio of the number of persons each determined as having a disease relative to the number of healthy subjects who received the test (that is, the ratio of the number of persons of the negative case determined erroneously as being positive). The positive case rates (sensitivity) and the false positive case rates (1-specificity) in the case of the cutoff value being changed were obtained based on data of the healthy subjects and the keratoconus patients classified in step S2 as the regression equation generating group.

The logit value obtained when the AUC (area under the curve) in the ROC curve indicated a greater value (that is, a value closer to 1) was set as a final cutoff value. More specifically, when the logit value in the case of a Youden index, that is, (sensitivity+specificity−1) being the greatest was set as the cutoff value, the final cutoff value was −0.4356. When this value was converted to the probability according to equation 4, the probability was 39.28%. The AUC of the ROC curve in the case of the cutoff value being −0.4356 (39.28%), was 0.8997 (standard error: 0.02495, 95% confidence interval: 0.8508 to 0.9486), and the sensitivity and the specificity were 82.19% and 84.27%, respectively. The AUC represents an area below the ROC curve.

Next, whether the regression equation evaluating group classified in step S2 had keratoconus or was a normal case, was determined by using the regression equation (equation 3) and the cutoff value (39.28%) obtained in steps S3 and S4, thereby evaluating the regression equation and the cutoff value (step S5). As a result, the sensitivity was 100% and the specificity was 76.06%. Whether the regression equation evaluating group had keratoconus or was a normal case was determined by changing the cutoff value to 50%. In this case, the sensitivity was 92.86% and the specificity was 84.44%. As described above, equation 3 was able to be derived by the multiple logistic regression analysis, and it was found that whether or not a subject eye had keratoconus was able to be determined with high accuracy (the sensitivity of 100% and the specificity of 76.06% (in the case of the cutoff value being 39.28%)) according to the equation 3. The regression coefficient of the steep meridian refractive power had a positive value (specifically, +1.707) and the odds ratio was greater (specifically, 5.510) than 1. Therefore, it was found that the steep meridian refractive power was such a parameter as to increase the probability p of keratoconus according to increase of the steep meridian refractive power, that is, a parameter promoting determination as keratoconus and having a positive correlation with probability p. The regression coefficient of the flat meridian refractive power had a negative value (specifically, −0.997) and the odds ratio was less (specifically, 0.369) than 1. Therefore, it was found that the flat meridian refractive power was such a parameter as to reduce the probability p of keratoconus according to increase of the flat meridian refractive power, that is, a parameter suppressing determination as keratoconus and having a negative correlation with the probability p. The regression coefficient of the with-the-rule astigmatism had a negative value (specifically, −3.481) and the odds ratio was less (specifically, 0.031) than 1. Therefore, it was found that the with-the-rule astigmatism was such a parameter as to reduce the probability p of keratoconus as compared with the astigmatisms (against-the-rule astigmatism, oblique astigmatism) other than the with-the-rule astigmatism, that is, a parameter suppressing determination as keratoconus and having a negative correlation with the probability p. In other words, it was found that the against-the-rule astigmatism or the oblique astigmatism was more likely to promote determination as keratoconus.

Furthermore, the regression coefficient (−3.481) of the with-the-rule astigmatism was greater than the regression coefficient (−0.997) of the flat meridian refractive power in the negative direction, and the odds ratio (value less than 0.1) of the with-the-rule astigmatism was less than the odds ratio (greater than 0.1 and less than 1) of the flat meridian refractive power. Thus, it was found that, as compared with the flat meridian refractive power, determination as to presence or absence of the with-the-rule astigmatism exerted a greater influence on determination of absence of keratoconus and was more likely to deny the presence of keratoconus.

Figure 2:
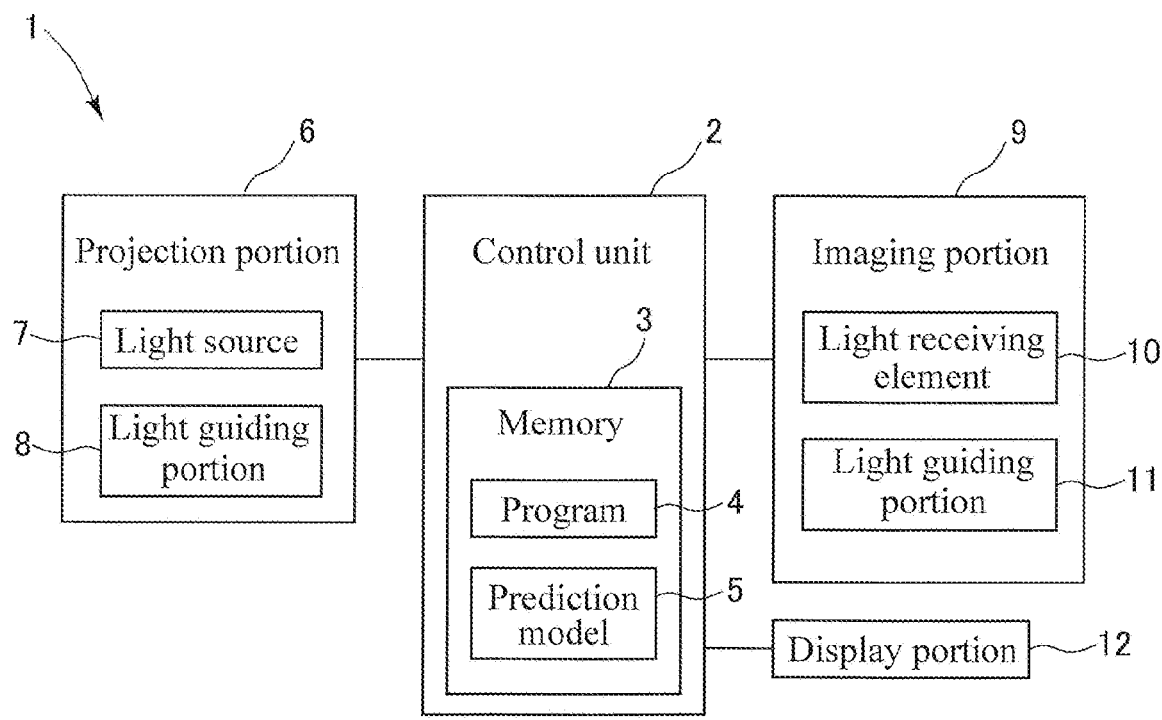
FIG. 2 is a block diagram illustrating a schematic configuration of a keratometer.

FIG. 2 illustrates a schematic configuration of a keratometer 1 based on the finding from the multiple logistic regression analysis. Hereinafter, the configuration of the keratometer 1 will be described. The keratometer 1 is a device for performing a test for a cornea to obtain a curvature radius, a refractivity, and a meridian direction of the cornea of an eye to be tested. The keratometer 1 has a memory 3 that stores a prediction model 5 for keratoconus, and also has a function of determining whether or not a subject eye is suspected of having keratoconus based on the prediction model 5, in addition to having a function similar to a function of a standard auto keratometer.

Specifically, the keratometer 1 includes a projection portion 6 for projecting single ring light 30 (see FIG. 4) or a plurality of dot-like light beams which are arranged into a ring-like shape, on the corneal surface 20 of an eye to be tested, an imaging portion 9 for taking a reflected image, on the corneal surface 20, of the ring light 30, a display portion 12 as an output potion for outputting a measurement result and the like, and a control unit 2 connected to these portions. The projection portion 6 has a light source 7 for emitting infrared light, and a light guiding portion 8 for guiding light from the light source 7, to a portion near the center O of the corneal surface 20 so as to project the light as the ring light 30 having the predetermined diameter d (for example, about 3 mm). The light guiding portion 8 includes a lens, a mirror, and the like. The keratometer 1 also has a mechanism (not shown) for performing alignment (adjustment) of an optical system of the keratometer 1 such that the ring light 30 is projected on a region near the center O of the corneal surface 20. The alignment mechanism includes a projection portion for projecting light for the alignment on the corneal surface 20, an imaging portion for taking a reflected image of the light for the alignment, and a driving portion for moving the optical system of the keratometer 1 based on the position of the reflected image. In the alignment state, the optical axis of the keratometer 1 coincides with the optical axis of the eye to be tested, and the center of the ring light 30 coincides with the center O of the corneal surface 20.

The imaging portion 9 includes a light receiving element 10 such as a CCD (charge coupled device) that receives the reflected light of the ring light 30, and a light guiding portion 11 that guides the reflected light of the ring light 30 to the light receiving element 10. The light guiding portion 11 includes a lens, a mirror, and the like. A positional relationship between the projection portion 6 and the imaging portion 9 is determined such that the reflected image of the ring light 30 is formed on the light receiving element 10.

The display portion 12 is, for example, a liquid crystal display, or may be another kind of display.

The control unit 2 has a configuration similar to that of a standard computer having a CPU, a ROM, a RAM, and the like. The control unit 2 controls the projection portion 6, the imaging portion 9, and the display portion 12 and performs, for example, processing of calculating kerato values. The control unit 2 includes the non-volatile memory 3 such as a ROM. For example, a program 4 for processes to be executed by the control unit 2 and the prediction model 5 for keratoconus are stored in the memory 3. The memory 3 is a non-transitory tangible storage medium for storing a computer-readable program and data in a non-transitory manner. The non-transitory tangible storage medium is implemented by a semiconductor memory, a magnetic disk, or the like. The control unit 2 performs processing by the CPU of the control unit 2 executing the program 4 stored in the memory 3 as the non-transitory tangible storage medium.

The prediction model 5 is structured to include the regression equation and the cutoff value obtained in steps similar to those in the multiple logistic regression analysis shown in FIG. 1. The regression equation of the prediction model 5 is specifically represented by the following equation 5.

$$\text{logit value} = \log(p/(1-p)) = \alpha + \beta_1 x_1 + \beta_2 x_2 + \beta_3 x_3 \quad \text{(Equation 5)}$$

The variable, coefficient, and constant in equation 5 are equivalent to those in equation 3. That is, p represents the probability of keratoconus, p=1 indicates that a subject eye has keratoconus, and p=0 indicates a normal case. $x_1$ represents the steep meridian refractive power (the unit is diopter D). $x_2$ represents the flat meridian refractive power (the unit is diopter D). $x_3$ represents a variable indicating whether or not the subject eye has a with-the-rule astigmatism (1 indicates that the subject eye has a with-the-rule astigmatism, and 0 indicates the other cases). a represents a constant, and is, for example, the same value (−30.791) as in equation 3. $\beta_1$ represents the regression coefficient of the steep meridian refractive power, is, for example, a positive value, and is, for example, the same value (+1.707) as in equation 3. $\beta_2$ represents the regression coefficient of the flat meridian refractive power, is, for example, a negative value, and is, for example, the same value (−0.997) as in equation 3. $\beta_3$ represents the regression coefficient indicating whether or not the subject eye has a with-the-rule astigmatism, is, for example, a negative value, is, for example, a value greater than the regression coefficient $\beta_2$ of the flat meridian refractive power in the negative direction, and is, for example, the same value (−3.481) as in equation 3. The odds ratio of the steep meridian refractive power is greater than 1. The odds ratio of the flat meridian refractive power is greater than 0.1 and less than 1. The odds ratio of the with-the-rule astigmatism is less than 0.1.

The cutoff value of the prediction model 5 may be a logit value in the case of the Youden index (sensitivity+specificity−1) being the greatest similarly to step S4 in FIG. 1, or the cutoff value may be another value. When the cutoff value is reduced, the sensitivity increases and the specificity is reduced. In contrast, when the cutoff value increases, the sensitivity is reduced and the specificity increases. The cutoff value can be determined as appropriate according to the sensitivity and the specificity.

The keratometer 1 does not have a function of performing corneal shape analysis (corneal topography). The keratometer 1 may have a function as a refractometer, that is, a function of measuring a refracted state of the entirety of the eye, in addition to having a kerato measuring function. In the refractometer, a target is projected on an ocular fundus, and a refracted state of the eye is measured based on the reflected image.

Next, the process performed by the control unit 2 will be described. The control unit 2 performs the process shown in FIG. 3 based on the program 4 stored in the memory 3. The process in FIG. 3 is started when, for example, a start switch (not shown) of the keratometer 1 is operated. When starting the process shown in FIG. 3, the control unit 2 firstly causes the projection portion 6 to project the ring light 30 (see FIG. 4) on the corneal surface 20 of an eye to be tested (step S11). Next, the control unit 2 causes the imaging portion 9 to take a reflected image of the ring light 30, and obtains the taken image data from the imaging portion 9 (step S12).

Next, kerato values are calculated based on the reflected image that is represented by the taken image data having been obtained (step S13). Specifically, as the kerato values, the curvature radius at the steep meridian 21, the curvature radius at the flat meridian 22, and a direction (angle) of each of the meridians 21 and 22 are obtained at the position of the ring light 30 on the corneal surface 20. The reflected image of the ring light 30 has a shape corresponding to the curvature of the corneal surface 20. Specifically, the light 30 is reflected in such a direction that an angle relative to the optical axis L is great at the position of the steep meridian 21 where the curvature radius is small (curvature is great) whereas the light 30 is reflected in such a direction that an angle relative to the optical axis L is small at the position of the flat meridian 22 where the curvature radius is great (curvature is small). As a result, the reflected image obtained by the imaging portion 9 has an ellipsoidal shape. The control unit 2 approximates, as in, for example, Japanese Laid-Open Patent Publication No. S61-146227, the reflected image obtained by the imaging portion 9 to an ellipsoidal shape, and obtains the major axis length, the minor axis length, the direction of the major axis, the direction of the minor axis, and the center position of the ellipsoidal shape. Based on these values, the curvature radius at the steep meridian 21, the curvature radius at the flat meridian 22, and the directions of the meridians 21 and 22 are obtained.

The control unit 2 obtains the refractive power (steep meridian refractive power) at the steep meridian 21 as the kerato value based on the curvature radius at the steep meridian 21. Similarly, the control unit 2 obtains the refractive power (flat meridian refractive power) at the flat meridian 22 based on the curvature radius at the flat meridian 22. The refractive power can be obtained from the curvature radius, the refractive index (for example, 1.376) of the cornea, and the refractive index (for example, 1.000) of air.

The control unit 2 also obtains, as the kerato value, the mean refractive power of the steep meridian refractive power and the flat meridian refractive power, and a cornea astigmatism power that is a difference between the steep meridian refractive power and the flat meridian refractive power.

Next, a predicted value of the keratoconus is calculated based on the prediction model 5 stored in the memory 3 and the kerato values calculated in step S13 (step S14). Specifically, the steep meridian refractive power obtained in step S13 is assigned to the independent variable $x_1$ in equation 5. The flat meridian refractive power obtained in step S13 is assigned to the independent variable $x_2$ in equation 5.

The control unit 2 determines whether the angle of the steep meridian obtained in step S13 is an angle (greater than or equal to 60 degrees and less than 120 degrees) classified as a with-the-rule astigmatism or another angle in order to assign a value to the independent variable $x_3$ in equation 5. When the angle is classified as a with-the-rule astigmatism, 1 is assigned to the independent variable $x_3$. When the angle is the other angle, 0 is assigned thereto. The logit value that is the dependent variable in equation 5 is obtained, and converted to the probability p according to equation 4, and the probability p is determined as a predicted value of keratoconus.

Next, whether or not the subject eye is suspected of having keratoconus is determined according to comparison between the predicted value p obtained instep S14 and a predetermined cutoff value (step S15). At this time, when the predicted value p is greater than the cutoff value, the subject eye is determined to be suspected of having keratoconus. When the predicted value p is less than or equal to the cutoff value, the subject eye is determined as a normal case.

Next, the display portion 12 displays each kerato value obtained in step S13 and the determination result in step 15, as the measurement result (step S16). At this time, when the determination in step S15 indicates that the subject eye is suspected of having keratoconus, the display portion 12 displays characters, a sign, or the like indicating that the subject eye is determined to be suspected of having keratoconus.

As described above, in this embodiment, keratoconus is determined based on the logistic regression equation represented by equation 5. In equation 5, as independent variables, only three parameters that are the steep meridian refractive power, the flat meridian refractive power, and the angle of the steep meridian which are obtained by a standard keratometer are used. Therefore, keratoconus can be more easily determined as compared with corneal topography in which corneal curvatures are measured at multiple points. The keratometer can also be installed at an optician's office, and keratoconus risk evaluation can be made very early before a patient consults with an ophthalmologist, and consulting with an ophthalmologist can be promoted.

This disclosure has been described according to the embodiment. However, it is to be understood that this disclosure is not limited to the above-described embodiment and structure. This disclosure also includes various modifications and modifications in the equivalent range. In addition, various combinations and modes, other combinations and modes structured by only one element being added to the various combinations and modes, and other combinations and modes structured by a wider or narrower range of components of the various combinations and modes are also included in the scope and the idea of this disclosure.

For example, equation 3 is derived as the prediction model for keratoconus, based on data of 124 keratoconus patients and 198 healthy subjects. However, the prediction model can be improved by adding cases of more patients in the future. Equation 3 is derived mainly based on data of persons at younger ages. However, equation 3 may be improved for persons in a wider range of ages. In this case, for example, the actual measurement data used for generating and evaluating the prediction model may include data of aged persons, the prediction model may be generated for each age group, or an age may be incorporated in the independent variable of the prediction model.

In the above-described embodiment, the result of comparison between the cutoff value and the probability p, of keratoconus, which is an output value of the prediction model is outputted to the display portion. However, the probability p itself may be outputted. In this case, a person who performs the test may determine whether or not the subject eye is suspected of having keratoconus based on the value of the probability p, to notify a person who has been tested of the determination result.

The three parameters that are the steep meridian refractive power, the flat meridian refractive power, and data indicating whether or not the subject eye has a with-the-rule astigmatism are used as the independent variables of the prediction model. However, other parameters which can be measured by a keratometer may be incorporated as the independent variables of the prediction model. Specifically, since the refractive power and the curvature radius can be considered to be equivalent to each other, the curvature radius at the steep meridian on the corneal surface, instead of the steep meridian refractive power, may be incorporated in the prediction model. The curvature radius at the flat meridian on the corneal surface, instead of the flat meridian refractive power, may be incorporated in the prediction model. Furthermore, instead of the dummy variable indicating whether or not the subject eye has a with-the-rule astigmatism, the dummy variable indicating whether or not the subject eye has an against-the-rule astigmatism or the dummy variable indicating whether or not the subject eye has an oblique astigmatism may be incorporated in the prediction model. The angle itself of the steep meridian or the angle itself of the flat meridian may be incorporated in the prediction model. When the number of the cases increases, the prediction model which uses, as the independent variables, only two parameters among the refractive power or the curvature radius at the steep meridian, the refractive power or the curvature radius at the flat meridian, and an angle of the steep meridian or the flat meridian, may be adopted. Furthermore, in the prediction model, in addition to at least two parameters among the refractive power or the curvature radius at the steep meridian, the refractive power or the curvature radius at the flat meridian, and an angle of the steep meridian or the flat meridian, another parameter (for example, the thickness of the cornea, a parameter obtained by measurement by a refractometer, ocular tension, age, and sex) may be adopted as the independent variable.

Furthermore, the prediction model may be generated by using a regression analysis method other than the logistic regression analysis such that a parameter obtained by a keratometer is set as the independent variable, and the probability of keratoconus is set as the dependent variable.

In the above-described embodiment, the logistic regression equation is incorporated in the keratometer. However, a table or a map indicating correspondence between presence or absence of keratoconus and the values of the independent variables (the steep meridian refractive power, the flat meridian refractive power, data indicating whether or not the subject eye has a with-the-rule astigmatism) may be previously obtained based on the logistic regression equation and the cutoff value before incorporation into the keratometer, and the obtained table or map may be incorporated in the keratometer, and the control unit of the keratometer may determine whether or not a subject eye has keratoconus, based on the table or the map.

In the above-described embodiment, the keratometer 1 corresponds to a keratoconus determination apparatus. The projection portion 6, the imaging portion 9, and the control unit 2 that perform steps S11 to S13 in FIG. 3 correspond to an obtaining portion. The control unit 2 that performs steps S14 and S15 corresponds to a determination portion. The memory 3 corresponds to a storage portion and a computer-readable storage medium. The prediction model 5 corresponds to a relational expression.

DESCRIPTION OF THE REFERENCE CHARACTERS 1 keratometer
2 control unit
3 memory
4 program
5 prediction model
6 projection portion
9 imaging portion
12 display portion
20 corneal surface
21 steep meridian
22 flat meridian
30 ring light

What is claimed is:

1. A keratoconus determination apparatus comprising:
   an obtaining portion configured to obtain values including a first refractive power at a steep meridian of a cornea of an eye to be tested, a second refractive power at a flat meridian of the cornea, and an angle of the steep meridian;
   a storage portion configured to store a logistic regression equation in which the first refractive power, the second refractive power and a dummy variable indicating a classification of astigmatism determined based on the angle of the steep meridian are three independent variables and an output value indicating likelihood of keratoconus is a dependent variable; and
   a determination portion configured to determine whether or not the eye to be tested has keratoconus, based on the output value indicating likelihood of keratoconus according to the logistic regression equation.

2. The keratoconus determination apparatus according to claim 1, wherein the dummy variable indicates whether or not an angle of the steep meridian is an angle classified as a with-the-rule astigmatism, a first regression coefficient of the first refractive power at the steep meridian is a positive value, a second regression coefficient of the second refractive power at the flat meridian is a negative value, and a third regression coefficient of the dummy variable is a negative value.

3. The keratoconus determination apparatus according to claim 2,
   wherein the first regression coefficient is +1.707, the second regression coefficient is −0.997, and the third regression coefficient is −3.481.

4. The keratoconus determination apparatus according to claim 3, where the determination portion determines whether or not an eye has keratoconus, according to a comparison between a predetermined cutoff value and the output value obtained by substituting, into the logistic regression equation, the values obtained by the obtaining portion.

5. A computer-readable storage medium having stored therein a program for causing a computer to perform:
   obtaining a first refractive power at a steep meridian of a cornea of an eye to be tested, a second refractive power at a flat meridian of the cornea, and an angle of the steep meridian;
   storing a logistic regression equation in which the first refractive power, the second refractive power and a dummy variable indicating a classification of astigmatism determined based on the angle of the steep meridian are three independent variables and an output value indicating likelihood of keratoconus is a dependent variable; and
   determining whether or not the eye to be tested has keratoconus, based on the output value indicating likelihood of keratoconus according to the logistic regression equation.

\* \* \* \* \*